(12) United States Patent
Choy et al.

(10) Patent No.: US 8,729,334 B2
(45) Date of Patent: May 20, 2014

(54) METHOD FOR DETERMINING GENOTOXICITY USING NON-FLUORESCENT PROTEINS

(75) Inventors: Hyon El Choy, Seoul (KR); Seok-Yong Choi, Gwangju (KR)

(73) Assignee: Industry Foundation of Chonnam National University, Gwangju (KR)

( * ) Notice: Subject to any disclaimer, the term of this patent is extended or adjusted under 35 U.S.C. 154(b) by 0 days.

(21) Appl. No.: 13/578,183

(22) PCT Filed: Mar. 31, 2011

(86) PCT No.: PCT/KR2011/002210
§ 371 (c)(1),
(2), (4) Date: Aug. 9, 2012

(87) PCT Pub. No.: WO2011/122864
PCT Pub. Date: Oct. 6, 2011

(65) Prior Publication Data
US 2013/0024955 A1    Jan. 24, 2013

(30) Foreign Application Priority Data
Mar. 31, 2010  (KR) .................. 10-2010-0029482

(51) Int. Cl.
*A61K 49/00* (2006.01)
*C12N 15/12* (2006.01)

(52) U.S. Cl.
USPC ............................................ 800/3; 536/23.5

(58) Field of Classification Search
CPC ........... G01N 33/5088; C12N 15/8509; A61K 49/0008
See application file for complete search history.

(56) References Cited

U.S. PATENT DOCUMENTS

2007/0087364 A1   4/2007   Shuga et al.
2008/0064053 A1   3/2008   Walmsley et al.

OTHER PUBLICATIONS

Amanuma et al. (Nature Biotechnology. 2000; 18: 62-65).*
Gurskaya et al. (Biochem. J. 2003; 373: 403-408).*
Gabor Mocz (Marine Biotechnology 2007; 9: 305-328).*
Amanuma et al., "Transgenic Zebrafish for Detecting Mutations Caused by Compounds in Aquatic Environments," Nature Biotechnol. 18:62-65, 2000.
Kosmehl et al., "A Novel Contact Assay for Testing Genotoxicity of Chemicals and Whole Sediments in Zebrafish Embyros," Environ. Toxicol. Chem. 25:2097-2106, 2006.
Theodorakis et al., "Relationship between Genotoxicity, Mutagenicity, and Fish Community Structure in a Contaminated Stream," J. Aquatics Ecosystem Stress and Recovery 7:131-143, 2000.
International Search Report from International Application No. PCT/KR2011/002210, dated Jan. 12, 2012 (date of completion of search) and Jan. 13, 2012 (date of mailing of report).

* cited by examiner

*Primary Examiner* — Scott Long
(74) *Attorney, Agent, or Firm* — Clark & Elbing LLP (57) ABSTRACT

The present invention relates to a method for determining a genotoxicity of a test substance, comprising the steps of: (a) transforming a fish with a nucleotide sequence encoding a non-fluorescent fluorescence protein with a mutation; (b) treating a test substance to the transformed fish; and (c) measuring a fluorescence in the test substance-treated fish, wherein the fluorescence is generated by reversion of the non-fluorescent fluorescence protein to the fluorescence protein due to a back mutation of the nucleotide sequence in the test substance-treated fish. According to the present invention, MutaFish system, Zebrafish (*Brachydanio rerio*) line, in which the fluorescence protein variant, preferably wild type EGFP variant ($EGFP^{mut}$) is transformed, provides a much excellent animal system for measuring a genotoxicity of a test substance via production of a fluorescent fry larvae generated through reversion of the fluorescent protein variant caused by treatment of the test substance. Accordingly, the MutaFish system of the present invention may determine a genotoxicity of a test substance in much more simple and high-throughput manner in an eukaryote to which the conventional methods (e.g., Ames test) may be not applied.

14 Claims, 4 Drawing Sheets

ATGGTGAGCAAGGGCGAGGAGCTGTTCACCGGGGTGGTGCCCATCCTGGTCGAG
CTGGACGGCGACGTAAACGGCCACAAGTTCAGCGTGTCCGGCGAGGGCGAGGGC
GATGCCACCTACGGCAAGCTGACCCTGAAGTTCATCTGCACCACCGGCAAGCTGC
                       GGGGGG in EGFP$^{mut\,2}$
                       GGGGG in EGFP$^{mut\,3}$
CCGTGCCCTGGCCCACCCTCGTGACCACCCTGACCTACGGCGTGCAGTGCTTCAG
CCGCTACCCCGACCACATGAAGCAGCACGACTTCTTCAAGTCCGCCATGCCCGAA
GGCTACGTCCAGGAGCGCACCATCTTCTTCAAGGACGACGGCAACTACAAGACCC
GCGCCGAGGTGAAGTTCGAGGGCGACACCCTGGTGAACCGCATCGAGCTGAAGG
GCATCGACTTCAAGGAGGACGGCAACATCCTGGGGCACAAGCTGGAGTACAACT
                CCC in EGFP$^{mut\,1}$
ACAACAGCCACAACGTCTATATCATGGCCGACAAGCAGAAGAACGGCATCAAGGT
GAACTTCAAGATCCGCCACAACATCGAGGACGGCAGCGTGCAGCTCGCCGACCA
CTACCAGCAGAACACCCCCATCGGCGACGGCCCCGTGCTGCTGCCCGACAACCAC
TACCTGAGCACCCAGTCCGCCCTGAGCAAAGACCCCAACGAGAAGCGCGATCAC
ATGGTCCTGCTGGAGTTCGTGACCGCCGCCGGGATCACTCTCGGCATGGACGAGC
TGTACAAGTAA

B

MVSKGEELFTGVVPILVELDGDVNGHKFSVSGEGEGDATYGKLTLKFICTTGKLPVPWP
TLVTTLTYGVQCFSRYPDHMKQHDFFKSAMPEGYVQERTIFFKDDGNYKTRAEVKFEG
DTLVNRIELKGIDFKEDGNILGHKLEYNYNSHNVYIMADKQKNGIKVNFKIRHNIEDGS
VQLADHYQQNTPIGDGPVLLPDNHYLSTQSALSKDPNEKRDHMVLLEFVTAAGITLG
MDELYK*

METHOD FOR DETERMINING GENOTOXICITY USING NON-FLUORESCENT PROTEINS

CROSS-REFERENCE TO RELATED APPLICATIONS

This application is the U.S. national stage filing under 35 U.S.C. §371 of international application PCT/KR2011/002210, filed Mar. 31, 2011, which claims benefit of Korean Patent Application No. 10-2010-0029482, filed Mar. 31, 2010.

BACKGROUND OF THE INVENTION

1. Field of the Invention

The present invention relates to a method for determining a genotoxicity using non-fluorescent fluorescence proteins.

2. Description of the Related Art

The introduction of chemicals into the environment represents a serious risk to environmental and human health. Therefore, current legislation in European and other industrial countries requires appropriate data on risk assessment for the registration of chemicals, pesticides, biocides and pharmaceuticals (Commission of the European Communities 1967, 1991, 1992, 1993a, b, 1994; CVMP/VICH 2000; EMEA/CHMP 2006; VICH 2004). Although various genotoxicity assays have been developed to assess toxicity of these chemicals, by far the most frequently used is the Ames assay (Ames, Durston, et al., 1973; Maron and Ames, 1983). This assay is based on the detection of reversal of point mutations in the his gene of a defective mutant of *Salmonella typhimurium* by quantifying the growth in cultures without histidine. The Ames assay has the critical disadvantage that *Salmonella* does not possess the cellular machinery of vertebrates which is necessary to convert procarcinogens into reactive metabolites. Thus, several transgenic animal systems including MutaMouse (Gossen, de Leeuw, et al., 1989), BigBlue mouse (Kohler, Provost, et al., 1991), gpt-Δ transgenic mouse systems (Nohmi, Katoh, et al., 1996), and rpsL transgenic zebrafish (Amanuma, Takeda, et al., 2000) have been developed. In all cases, however, transgenic reporter genes, all with prokaryotic origin, must be introduced and assessed in appropriate test bacteria, *E. coli*, after extraction of DNA from animal organs.

Throughout this application, various publications and patents are referred and citations are provided in parentheses. The disclosures of these publications and patents in their entities are hereby incorporated by references into this application in order to fully describe this invention and the state of the art to which this invention pertains.

SUMMARY OF THE INVENTION

The present inventors have made intensive studies to develop a novel method for determining a genotoxicity of a test substance. As results, we have developed a method (i.e., MutaFish model) for determining a genotoxicity of a test substance using a cell or zebrafish transformed with a fluorescing protein variant, preferably EGFP (enhanced green fluorescent protein) variant (EGFP$^{mut}$), and discovered that the MutaFish model allows the genotoxicity of the test substance to be visualized using the fluorescence of EGFP revertants, determining its genotoxicity in much more sensitive and feasible manner compared with conventional models.

Accordingly, it is an object of this invention to provide a method for determining a genotoxicity of a test substance.

It is another object of this invention to provide a composition for determining a genotoxicity of a test substance.

It is still another object of this invention to provide a wild type EGFP variant (EGFP$^{mut}$) sequence.

Other objects and advantages of the present invention will become apparent from the following detailed description together with the appended claims and drawings.

BRIEF DESCRIPTION OF THE DRAWINGS

NH$_2$-MVSKGEELFTGVVPILVELDGDVNGHKFSVSGEGEGDATYGKLTLKFICTTGGSCPCPGPPS-OH.

DETAILED DESCRIPTION OF THIS INVENTION

In one aspect of this invention, there is provided a method for determining a genotoxicity of a test substance, comprising the steps of: (a) transforming a fish with a nucleotide sequence encoding a non-fluorescent fluorescence protein with a mutation; (b) treating a test substance to the transformed fish; and (c) measuring a fluorescence in the test substance-treated fish, wherein the fluorescence is generated by reversion of the non-fluorescent fluorescence protein to the fluorescence protein due to a back mutation of the nucleotide sequence in the test substance-treated fish.

In another aspect of this invention, there is provided a composition for determining a genotoxicity of a test substance via detection of a back mutation, wherein the composition comprises a fish transformed with a nucleotide sequence encoding a non-fluorescent fluorescence protein with a mutation, and the back mutation is generated by treating the test substance to the transformed fish.

In still another aspect of this invention, there is provided a nucleotide sequence of SEQ ID NO:1 or SEQ ID NO:2 encoding a EGFP variant (EGFP$^{mut}$) or a complementary sequence thereof.

The present inventors have made intensive studies to develop a novel method for determining a genotoxicity of a test substance. As results, we have developed a method (i.e., MutaFish model) for determining a genotoxicity of a test substance using a cell or zebrafish transformed with a fluorescing protein variant, preferably EGFP (enhanced green fluorescent protein) variant (EGFP$^{mut}$), and discovered that the MutaFish model allows the genotoxicity of the test substance to be visualized using the fluorescence of EGFP revertants, determining its genotoxicity in much more sensitive and feasible manner compared with conventional models.

The short-term test methods have been developed to measure the extent to what a chemical compound is reacted with DNA or a chemical compound may modify DNA. Although the positive results using these methods are not sufficient to verify carcinogenicity of the chemical compound, these methods suggest the possibility of a causative factor, and thus have been often utilized to select a chemical compound by its quantification in an animal body. For example, the short-term test method includes a mutagenicity test (e.g., Ames test), a chromosome effect study (e.g., measurement of change in chromosome number or structure), a mammalian transformation assay (e.g., measurement of change in cells), and so forth.

Of them, Ames test is the most common method to assess a mutagenic potential of a chemical compound. According to Ames test, it is estimated to induce a back mutation of a particular gene in *Salmonella typhimurium* strains (i.e., revertants) treated with a chemical compound. It has been known that not less than 90% of the chemical compound shows carcinogenicity with a proviso that Ames test is positive in animal experiments. Ames test has several advantages of: (a) economical expense; (b) feasibleness; and (c) rapidity. Unfortunately, Ames test has fetal drawbacks as follows. Ames test may not reflect entirely cellular mechanisms in eukaryotes (e.g., a human being) since *Samonella* species used in Ames test belong to be a prokaryote. For example, *Samonella* may perform no cellular mechanism in vertebrates which is necessary to convert procarcinogens to reactive metabolites. Therefore, the present inventors have developed a novel method for determining a genotoxicity of a test substance using a non-fluorescent fluorescence protein to overcome the above-mentioned defects.

This invention provides a method for determining a genotoxicity of a test substance using a cell (e.g., *Samonella typhimurium* strain; CH4001 and CH4003 strain) or a fish (e.g., MutaFish) transformed with a wild-type EGFP variant (EGFP$^{mut}$).

In this specification, this invention provides a method for determining a genotoxicity of a test substance, comprising the steps of:

(a) transforming a cell or a fish with a nucleotide sequence encoding a non-fluorescent fluorescence protein with a mutation;

(b) treating a test substance to the transformed cell or fish; and (c) measuring a fluorescence in the test substance-treated cell or fish, wherein the fluorescence is generated by reversion of the non-fluorescent fluorescence protein to the fluorescence protein due to a back mutation of the nucleotide sequence in the test substance-treated cell or fish.

As described above, the most simple method to assess a test substance as a mutagen is to carry out a reversion experiment using an auxotropic bacterial mutant (for example, Ames test). The most feasible reversion experiment is to count the number of revertants produced by culturing certain number of bacterial mutants in mutagen-containing media. Where the test substance is a mutagen, the number of revertants cultured in mutagen-containing media is higher than that cultured in no mutagen-containing media.

The present inventors have developed a method for determining a genotoxicity of a test substance in much effective manner using a transformant (e.g., a cell or fish) transformed with a non-fluorescent fluorescence protein, wherein the method enables to visualize in much more feasible and high-throughput manner the fluorescence generated by reversion of the non-fluorescent fluorescence protein to the fluorescence protein. Accordingly, the present method is a much excellent method capable of overcoming limitations that the conventional methods (e.g., Ames test) utilizes a prokaryote and thus may be not applied to an eukaryote.

The term "mutated" or "mutation" used herein refers to a mutation generated in a nucleotide sequence encoding a non-fluorescent fluorescence protein capable of being used in the present invention, and preferably, a back mutation or revertant which contributes to reversion of a non-fluorescent fluorescence protein to a fluorescence protein in a transformed cell or fish.

In general, DNA mutation may be induced by diverse factors (e.g., UV, virus, transposon, mutagen, etc.), and by organism (e.g., hypermutation inside cell) in itself. In addition, mutation may result in various types of changes in DNA sequence, for example, including a nonsense mutation, a frameshift mutation, a missense mutation and so on. A missense mutation is a point mutation in which a single nucleotide is replaced or substituted to another nucleotide, resulting in a protein to be expressed according to a codon changed by the mutated nucleotide. A frameshift mutation is a genetic mutation caused by insertion or deletion of a number of nucleotides in which a protein to be expressed is determined according to a number of inserted or deleted nucleotides. A nonsense mutation is a point mutation in which a single nucleotide is mutated to another nucleotide, thereby frequently producing the protein without its original activity.

According to a preferable embodiment, the non-fluorescent fluorescence protein with a mutation utilized in the present invention is mutated by (i) a frameshift mutation or (ii) a missense mutation-producing substitution mutation in a nucleotide sequence of a wild type fluorescence protein. According to this invention, the mutation generated in the nucleotide sequence encoding the non-fluorescent fluorescence protein of the present invention includes aforementioned mutations. In particular, the mutation generated in the present invention includes various types of mutations induced in the nucleotide sequence encoding a non-fluorescent fluorescence protein by a test substance, leading to produce the fluorescence by reversion of a non-fluorescent fluorescence protein (variant) to a fluorescence protein. When the fluorescence is observed by reversion of a non-fluorescent fluorescence protein (variant) to a fluorescence protein, the test substance is determined to have a genotoxicity in a transformed cell or fish, suggesting a candidate substance, carcinogen.

According to a preferable embodiment, the back mutation of the present invention may revert to a fluorescence protein a non-fluorescent fluorescence protein with a frameshift mutation or with a substitution mutation. More preferably, the back mutation of the present invention may revert to a fluorescence protein a non-fluorescent fluorescence protein which is encoded by a nucleotide sequence of SEQ ID NO:1 or SEQ ID NO:2 encoding a EGFP variant (EGFP$^{mut}$) or a complementary sequence thereof. The term "substitution mutation" used herein refers to revert a non-fluorescent fluorescence protein to a fluorescence protein by mutation in the nucleotide sequence encoding the non-fluorescent fluorescence protein of the present invention, including a point mutation, insertion or deletion, and more preferably, a mutation induced by a missense mutation.

According to a preferable embodiment, the fluorescence protein useful in the method of the present invention includes, but not limited to, GFP (green fluorescent protein), RFP (red fluorescent protein), CFP (cyan fluorescent protein), YFP (yellow fluorescent protein), BFP (blue fluorescent protein), EGFP (enhanced green fluorescent protein), ECFP (enhanced cyan fluorescent protein), EYFP (enhanced yellow fluorescent protein), ERFP (enhanced red fluorescent protein), mCherry, mTomato and EBFP (enhanced blue fluorescent protein). Most preferably, the fluorescence protein of the present invention is EGFP.

According to a preferable embodiment, the EGFP$^{mut}$ of the present invention shows no fluorescence.

According to a preferable embodiment, the fish capable of being applied to the method of the present invention includes, Zebrafish, but not limited to.

According to a preferable embodiment, the method of the present invention further includes the step of obtaining a fry larvae by hatching the transformed fish-derived embryo after the step (b).

According to a preferable embodiment, the measurement of the fluorescence in the step (c) of the present invention may be carried out using diverse methods known to those ordinarily skilled in the art, and most preferably a flow cytometry.

According to more preferable embodiment, the present invention includes the screening method of mutagens including the steps of: (a) treating the transformed cell or fish as described above; and (b) measuring the fluorescence of the EGFP variants, wherein the test substance is determined as a mutagen where it may induce the fluorescence of wild type EGFP protein variant consisting of a nucleotide sequence of SEQ ID NO:1 or SEQ ID NO:2, or a complementary nucleotide sequence thereof.

Since the present method comprises the EGFP variant of this invention as active ingredients described above, the common descriptions between them are omitted in order to avoid undue redundancy leading to the complexity of this specification.

Figure 2:
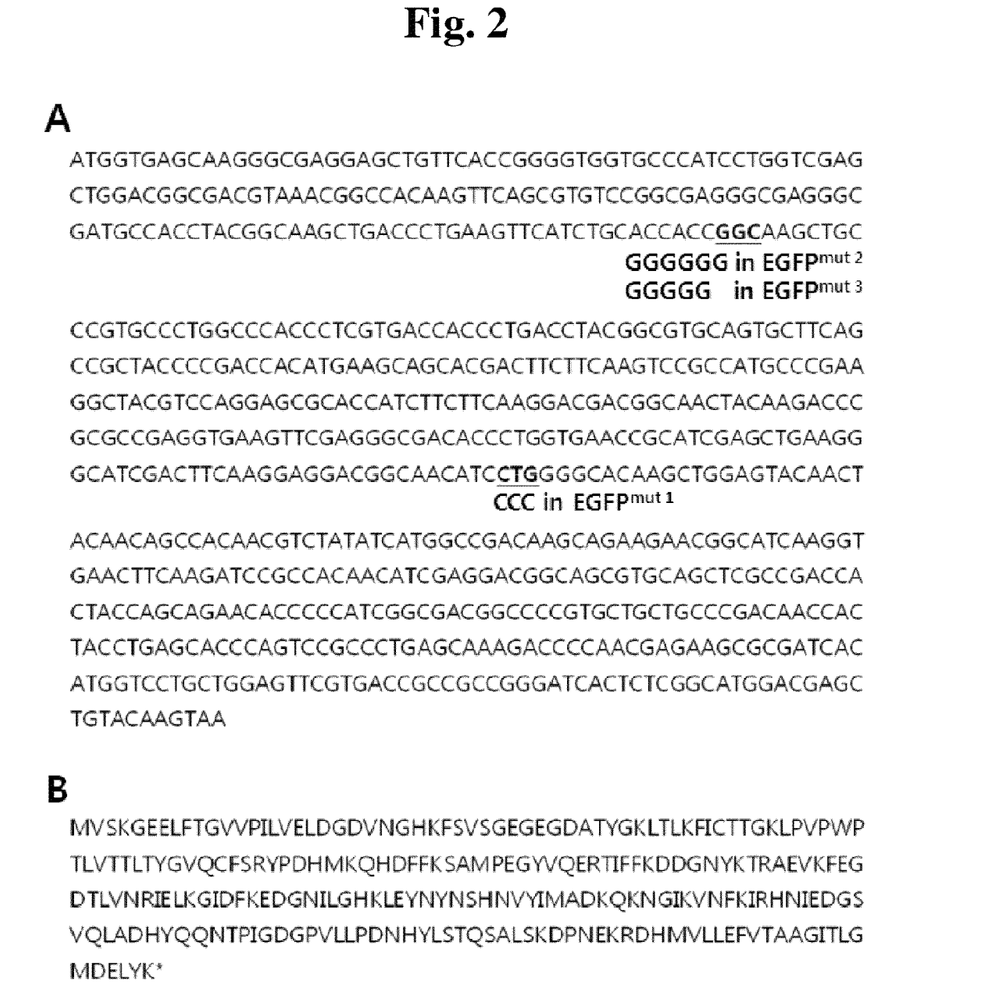
FIG. 2 shows DNA (A) and amino acid sequence (B) of wild-type EGFP, in which DNA sequence of EGFP$^{mut}$ is indicated. EGFP$^{mut1}$ includes the substitution of Pro for Leu at position 137 [L137P (CTG to CCC)], and EGFP$^{mut2}$ is a mutation that Gly was added next to Gly at position 51 (TG51GKLPVPWPT). In addition, EGFP$^{mut3}$ is −1G frameshift mutation by adding two Guanosines next to Gly at position 51. Protein translation in EGFP$^{mut3}$ would be stopped after 62$^{nd}$ amino acid, ten amino acids after Gly at position 51. The amino acid sequence of EGFP$^{mut3}$ is as follows.

The term "test substance" used in the present screening method refers to a unknown substance which may generate a revertant by inducing a mutation in a variety of nucleotide sequences encoding a non-fluorescent fluorescence protein or complementary nucleotide sequences thereof, or the non-fluorescent fluorescence protein having the amino acid sequence encoded by the above-mentioned nucleotide sequences, and more preferably, a unknown substance generating the fluorescence protein by inducing a mutation in a wild type EGFP variant (EGFP$^{mut}$) protein including a nucleotide sequence of SEQ ID NO:1 or SEQ ID NO:2 represented in FIG. 2 or a complementary nucleotide sequence thereof, or an amino acid sequence consisting of SEQ ID NO:3 or SEQ ID NO:4.

Next, the mutation of the non-fluorescent fluorescence protein to the fluorescence protein may be detected via measurement of fluorescence in the test-substance-treated cell or fish. More preferably, the reversion of non-fluorescence to fluorescence is measured in the aforementioned wild type EGFP protein variant (EGFP$^{mut}$) protein.

The test substance analyzed according to the present screening method may be obtained from libraries of synthetic or natural compounds, or natural substances. The method to prepare the library of such compounds is well-known in the art. The library of synthetic compounds may be commercially purchased from Maybridge Chemical Co. (UK), Comgenex (USA), Brandon Associates (USA), Microsource (USA) and Sigma-Aldrich (USA), and the library of natural compounds may be commercially purchased from Pan Laboratories (USA) and MycoSearch (USA).

The test substance may be obtained from various combination library methods known to those ordinarily skilled in the art, for example, including a biological library, a spatially addressable parallel solid phase or solution phase library method, a synthetic library method in which deconvolution is required, a "1-bead 1-compound" library method, and a synthetic library method using an affinity chromatography for selection. The synthetic method of a molecule library is disclosed in DeWitt et al., *Proc. Natl. Acad. Sci. U.S.A.* 90, 6909, 1993; Erb et al., *Proc. Natl. Acad. Sci. U.S.A.* 91, 11422, 1994; Zuckermann et al., *J. Med. Chem.* 37, 2678, 1994; Cho et al., *Science* 261, 1303, 1993; Carell et al., *Angew. Chem. Int. Ed. Engl.* 33, 2059, 1994; Carell et al., *Angew. Chem. Int. Ed. Engl.* 33, 2061; and Gallop et al., *J. Med. Chem.* 37, 1233, 1994.

Meanwhile, the present invention provides a cell transfected with a recombinant vector including the EGFP variant or a transcript thereof, and a transformed cell via a gene introduction, or a transformant thereof.

Since the present transformed cells or transformants include the EGFP variant described above as an active ingredient, the common descriptions between them are omitted in order to avoid undue redundancy leading to the complexity of this specification.

The recombinant vector of the present invention includes the nucleotide sequence of SEQ ID NO:1 or SEQ ID NO:2, or the complementary nucleotide sequence thereof. Typically, the recombinant vector of this invention may be constructed as cloning or expression vector. In addition, the vector of this invention may be constructed using a prokaryotic or eukaryotic cell as a host cell.

Preferably, the recombinant vector of the present invention includes (i) a nucleotide sequence encoding an expression target substance of the present invention; (ii) a promoter which is operatively linked to the nucleotide sequence of (i) and generates a RNA molecule in animal cells, and more preferably, (i) a nucleotide sequence encoding a nucleotide sequence of SEQ ID NO:1 or SEQ ID NO:2 of the present invention, or a complementary nucleotide sequence thereof; (ii) a promoter which is operatively linked to the nucleotide sequence of (i) and generates a RNA molecule in animal cells; and (iii) 3'-untranslated region responsible of 3'-terminal polyadenylation of the RNA molecule in animal cells.

Preferably, the expression target substance includes a non-fluorescent fluorescence protein which is mutated from a fluorescence protein including GFP, RFP, CFP, YFP, BFP, EGFP, ECFP, EYFP, ERFP and EBFP, but not limited to. Most preferably, the fluorescence protein is EGFP.

The term "promoter" used herein means a DNA sequence regulating a coding sequence (CDS) or an expression of a functional RNA. The expression target substance-encoding nucleotide sequence is operatively linked to the promoter in the recombinant vector of the present invention. The term "operatively linked" used herein refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The present vector which is expression vector and utilizes a prokaryotic cell as a host commonly includes a strong promoter (e.g., tac promoter, lac promoter, lacUV5 promoter, lpp promoter, $p_L^\lambda$ promoter, $p_R^\lambda$ promoter, rac5 promoter, amp promoter, recA promoter, SP6 promoter, trp promoter, T7 promoter, etc.) for transcription, a ribosome-binding site for translation, and transcription/translation termination sequence. Much more preferably, the host cell capable of being utilized in the present invention includes *Samonella*, and most preferably, *Samonella typhimurium* LT2 strain. In this connection, it is preferable that the promoter useful in the present invention is lac promoter. The promoter and operator region of *E. coli* tryptophan biosynthesis pathway (Yanofsky, C., *J. Bacteriol.*, 158: 1018-1024 (1984)), and $p_L^\lambda$ promoter (Herskowitz, I. and Hagen, D., *Ann. Rev. Genet.*, 14: 399-445 (1980)) may be used as a regulatory region in *E. coli* utilized as a host. Meanwhile, the vector capable of being used in the present invention may be prepared by manipulating a plasmid (example: pSC101, ColE1, pBR322, pUC8/9, pHC79, pUC19, pET, etc.), a phage (example: λgt4λB, λ-Charon, λΔz1, M13, etc.) or a virus (example: SV40, etc.) known to those ordinarily skilled in the art.

The procedure to deliver the present vector into a cell may be carried out according to various methods known to those ordinarily skilled in the art. For example, the transformation using a prokaryotic cell as a host may be performed according to a $CaCl_2$ method (Cohen, S. N. et al., *Proc. Natl. Acac. Sci. USA*, 9: 2110-2114 (1973)), a Hanahan method (Cohen, S. N. et al., *Proc. Natl. Acac. Sci. USA*, 9:2110-2114 (1973); and Hanahan, D., *J. Mol. Biol.*, 166: 557-580 (1983)) and an electroporation method (Dower, W. J. et al., *Nucleic. Acids Res.*, 16: 6127-6145 (1988)).

Meanwhile, the promoter capable of being utilized in the present invention when the recombinant vector of the present invention is applied to a mammalian such as a fish may operate in an animal cell, more preferably a mammalian cell, and thus regulate the transcription of the expression target substance of the present invention. The promoter includes a promoter derived from a mammalian virus and a genome of a mammalian cell, for example including, but not limited to, CMV (cytomegalo virus) promoter, adenovirus late promoter, vaccinia virus 7.5K promoter, SV40 promoter, HSV tk promoter, RSV promoter, human elongation factor 1α (hEF1α) promoter, methallothionein promoter, β-actin promoter, human IL-2 gene promoter, human IFN gene promoter, human IL-4 gene promoter, human lymphotoxin gene promoter and human GM-CSF gene promoter. Most preferably, the promoter capable of being utilized in the present invention includes CMV promoter or hEF1α promoter. Preferably, the expression construct used in the present invention includes a polyadenylation sequence (for example, bovine hormone terminator and SV40-derived polyadenylation sequence).

In more detail, the present recombinant vector for transformation includes a construct of "promoter-expression target substance-encoding nucleotide sequence-polyadenylation sequence", and more preferably, "CMV promoter-non-fluorescent fluorescence protein-SV40-derived polyadenylation sequence. In addition, the recombinant vector for transformation may be prepared using Multisite Gateway-based construct kit (Fisher, et al., 2006; Kwan, et al., 2007) to include a transposon element in both ends of the construct. The prepared recombinant vector is microinjected into fertilization eggs derived from Zebrafishes, and more preferably, fertilization eggs of a single-cell stage (Xu, Q. (1999). Microinjection into zebrafish embryos. In "Molecular Methods in Developmental Biology" (M. Guille, Ed.), Vol. 127, pp. 125-132. Humana Press, Inc., Totowa, N.J.). The eggs of not more than 20 min after fertilization are microinjected in the present invention, and the F1 embryos from the microinjected eggs are raised to sexual maturity and mated each other, followed by obtaining F2 embryos for a homozygote expressing a transformed expression target substance. Subsequently, incross between F2 embryo zebrafishes is performed to obtain a F3 embryo.

The vector system of this invention may be performed by various methods known to those skilled in the art and its practical method is described in Sambrook et al., Molecular Cloning, A Laboratory Manual, Cold Spring Harbor Laboratory Press (2001), which is herein incorporated by reference.

The preparation of animal cells transformed with the recombinant vector of the present invention may be carried out using a conventional gene transfection method known to those ordinarily skilled in the art, for example including electroporation, liposome-mediated transfection (Wong, et al., 1980), retrovirus-mediated transfection (Chen, H. Y., et al., (1990), J. Reprod. Fert. 41: 173-182; Kopchick, J. J. et al., (1991) Methods for the introduction of recombinant DNA into chicken embryos. In Transgenic Animals, ed. N. L. First & F. P. Haseltine, pp. 275-293, Boston; Butterworth-Heinemann; Lee, M.-R. and Shuman, R. (1990) Proc. 4th World Congr. Genet. Appl. Livestock Prod. 16, 107-110) and microinjection (Zebrafish Course, Mullins, August, 2005; Xu, Q. (1999). Microinjection into zebrafish embryos. In "Molecular Methods in Developmental Biology" (M. Guille, Ed.), Vol. 127, pp. 125-132. Humana Press, Inc., Totowa, N.J.) and more preferably, microinjection.

The features and advantages of the present invention will be summarized as follows:

(a) The present invention relates to a method for determining a genotoxicity using a fluorescence protein variant, preferably wild type EGFP variant (EGFP$^{mut}$).

(b) According to the present invention, MutaFish system (*Danio rerio* line) into which the fluorescence protein variant, preferably wild type EGFP variant (EGFP$^{mut}$) is transformed, provides a much excellent animal system for measuring a genotoxicity of a test substance via production of a fluorescent fry larvae generated through reversion of the fluorescent protein variant caused by treatment of the test substance.

(c) The MutaFish system of the present invention may determine a genotoxicity of a test substance in much more simple and high-throughput manner in an eukaryote to which the conventional methods (e.g., Ames test) may be not applied.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods

*Salmonella* Strains

*S. typhimurium* strain of Ames test, TA98 and TA, were purchased and grown following manufacture's instruction (Xenometrix AG, Switzerland). CH4001 and CH4003 strains carrying EGFP$^{mut}$ DNA on their chromosomes (Table 1) were created as described in Result section.

TABLE 1

Stains and plasmids used in this invention.

| | Description | Reference |
|---|---|---|
| Strains | | |
| LT2 | Wild type *Salmonella typimurium* | |
| TA100 | Ames test strain | Barnes et al., (1982) |
| TA98 | Ames test strain | Isono & Yourno (1974) |
| CH4001 | TA100 carrying EGFP$^{mut1}$ on chromosome | this invention |
| CH4003 | TA98 carrying EGFP$^{mut3}$ on chromosome | this invention |
| Plasmids | | |
| pEGFP | Clontech Laboratories | Yang, Cheng et al., (1996) |
| pEGFP::CAT | carries CAT at stuI site of pEGFP | |
| pEGFP$^{mut1}$::CAT | carries leu$^{137}$ (CTC) to pro (CCC) change | this invention |
| pEGFP$^{mut2}$::CAT | carries GGG next to gly$^{51}$ (GGG) | this invention |
| pEGFP$^{mut3}$::CAT | carries GG next to gly$^{51}$(GGG) | this invention |
| pCMV-Mut-EGFP::pCMLC2-mCherry | carries relevant EGFP$^{mut}$ in Tol2kit | this invention |

Construction of EGFP$^{mut}$

Figure 1:
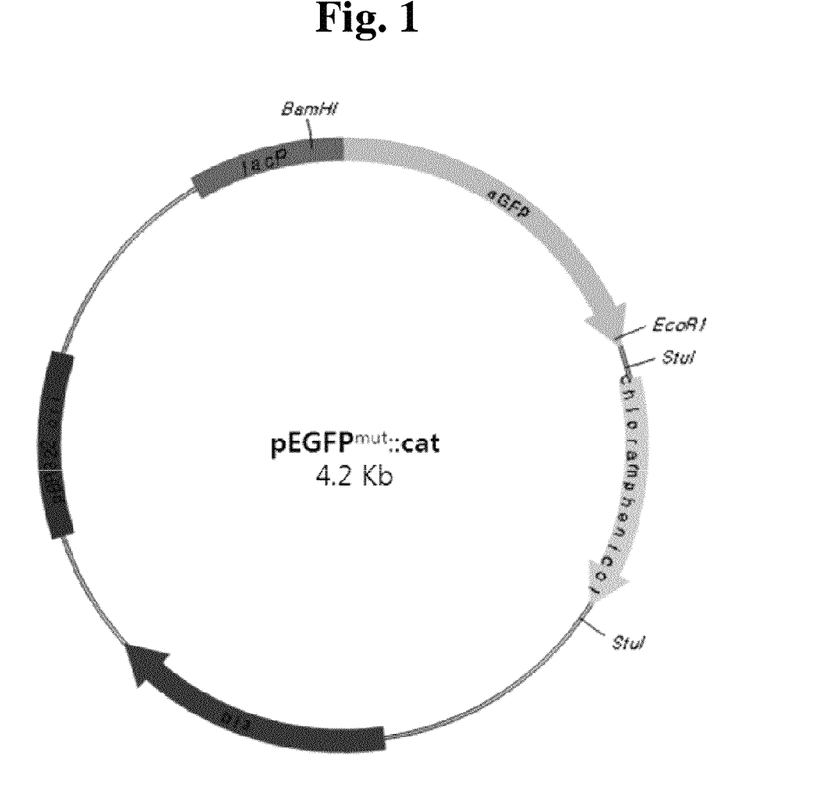
FIG. 1 represents a map of pEGFPmut::cat vector. The cat gene was cloned into stuI site of pEGFP vector (Clonetech).

The non-fluorescent mutant EGFP was obtained through site directed mutagenesis using primers with mutations indicated. Four sets of primers were used as follows: a forward primer (Primer 1) includes the BamHI site of the pEGFP (Clontech Laboratories, Palo Alto, Calif.) (Yang, Cheng, et al., 1996) upstream of the lac promoter; and a reverse primer (Primer 4) includes the EcoRI site downstream of the stop codon (Table 2). A second set of primers (Primer 2-x and Primer 3-x) that contains the desired mutation was designed to produce the necessary change in the nucleobases. (Joseph Sambrook, 2001). To construct EGFP$^{mut1}$, a first set of PCR (Standard 30 sec at 95° C., 30 sec at 55° C. and 1 min at 72° C./cycle) was carried out with primers 1 and 3d, and a second set of PCR Primers 2d and 4. To construction EGFP$^{mut2}$, a first set of PCR (Standard 30 sec at 95° C., 30 sec at 55° C. and 1 min at 72° C./cycle) was carried out with primers 1 and 3a, and a second set of PCR Primers 2a and 4. To construction EGFP$^{mut3}$, a first set of PCR (Standard 30 sec at 95° C., 30 sec at 55° C. and 1 min at 72° C./cycle) was carried out with primers 1 and 3b, and a second set of PCR Primers 2b and 4. The PCR product from the two reactions was mixed, optimized and annealed then subsequently used as the template for a final PCR set using primers 1 and 4. The final PCR product was digested with EcoRI and BamHI and re-ligated to a pEGFP empty vector. The plasmids carried the non-fluorescent EGFP gene under the control lac promoter. To place EGFP$^{mut}$ gene into *Salmonella* chromosome, chloramphenycol acetyl transferase (CAT) gene was cloned into StuI site of the plasmid, resulting in pEGFP$^{mut}$::CAT plasmid (FIG. 1). See, FIG. 2 for sequence alteration in EGFP$^{mut}$.

TABLE 2

Primers used for construction of EGFP$^{mut}$.

| | primer | Sequence (5'-3') | description |
|---|---|---|---|
| 1 | mEGFP-F | CCTGCAGGTCGACTCTAGAG | Top primer |
| 4 | mEGFP-R | CCGGCGCTCAGTTGGAATTC | Bottom primer |
| 2-a | G51GGG-F | ATCTGCACCACCGGGGGAAGCTG CCCGTGCCC | G51 + GGG (Gly-Gly) (Template for frameshift mutation) |
| 3-a | G51GGG-R | GGGCACGGGCAGCTTCCCCCCGGT GGTGCAGAT | |
| 2-b | G51GGG + G-F | CATCTGCACCACCGGGGGGAAGC TGCCCGTGCCC | G51 + GGG + G |
| 3-b | G51GGG + G-R | GGGCACGGGCAGCTTCCCCCCCGG TGGTGCAGATG | G51 + GGG + G |
| 2-f | L137P-F | CTCGTGACCACCCTGGCCTACGGCG TGCAGTGC | Base pair substitution |
| 3-f | L137P-R | GCACTGCACGCCGTAGGCCAGGGT GGTCACGAG | Base pari substitution |

Placement of EGFP$^{mut}$ DNA into *Salmonella* Chromosome

The EGFP$^{mut}$ DNA was inserted into the chromosome of *Salmonella typhimurium* LT2 strain via its putA site approximately 5 minutes away from the termination (ter) region of the chromosome (Elliott, 1992). lacP-EGFP$^{mut}$::CAT DNA was amplified with primers that contain sequences for the putA site of *S. enterica* serovar *Typhimurium*: 5'-primer GAAATCGCCTGTTAATGGTACCAATAGC-CTTGACGCAATAGAGTAATGACTCACTCACTC ATT-AGGCACCCCAGGCTTT and 3'-primer CGTCAT TGT-CAGTCTCTTACAGAAAGATTACACGATTATTTCATCG GCAGGAGACGCGTAGCACCA GGCGTTTAAG, which consisted of 50-nt or 55-nt of putA (putA sequences are underlined) and 25-nt or 22-nt sequences flaking lacP-non-EGFP::cat using pEGFP$^{mut}$::CAT plasmid as template. The 1.4-kbp PCR products were purified and transformed into bacteria carrying a Red helper plasmid (pKD46) by electroporation (Datsenko and Wanner, 2000). The Linear DNA contained a chloramphenicol gene as a marker for the P22 transduction into the *S. typhimurium* strain of Ames test, TA100 and TA98 to construct CH4001 and 4003, respectively (Davis, et al., 1980).

Ames Test

The plate-incorporation assay was carried out as described (OECD, 1997). Briefly, bacterial cells from stock cultures were grown for 12 hr in liquid medium at 37° C. A volume of 0.1 mL bacterial suspension was added to 2 mL of top agar (Difco) medium containing 0.6% agar, 0.6% NaCl and 20.96 µg of l-histidine and d-biotin (Sigma). Test solution (or solvent control, or positive control agent) and the S9-mix (0.5 mL/plate; 10% (v/v) S9) or potassium phosphate buffer (0.5 mL/plate; 0.2 M, pH 7.4; Sigma) were also added to the top agar which was then mixed and poured onto the top of Vogel-Bonner minimal medium agar plates (3 replicates/dose for the treated and 6 replicates for the solvent control). Colonies were counted 48 hr after incubation at 37° C. The highest volume of the test solution added per plate was initially limited to 100 µL, and then increased up to 200 µL in confirmation studies.

S9-Mix

Composition: One mL of S9-mix contained 0.1 mL of S9, 0.01 mL of 0.4 M $MgCl_2$ (Sigma), 0.01 mL of 1.65 M KCl (Sigma), 0.5 mL of 0.2 M phosphate buffer (pH 7.4; Sigma), 0.04 mL of 0.1 M NADP (Sigma), 0.005 mL of 1 M glucose-6-phosphate (Sigma) and 0.335 mL of distilled water. All co-factors were filtered through a 0.45-µm sterilizing membrane (Millipore) before use.

Preparation of Mutagens

A stock solution of 81 mM ENU was prepared by dissolving 1 g of ENU (isopack N-3385; Sigma Chemical Co., St. Louis, Mo.) into 105.5 ml of 0.008% Instant Ocean salts (Senju Pharmaceutical, Hyogo, Japan) buffered with 5 mM '2-(N-morpholino)ethanesulfonic acid (pH 6.0) and the solution was stored at −80° C. A stock solution of 2 mg/ml ICR-191 (Polyscience Inc., Warrington, Pa.,) was prepared by dissolving 20 mg of ICR-191 into 10 ml sterile distilled water.

Construction of Zebrafish Expression Vector Carrying EGFP$^{mut}$

EGFP$^{mut}$ gene in pEGFP$^{mut}$::CAT plasmid was PCR-amplified with forward and reverse primers containing attB1 and attB2, respectively. The sequence of the primers is as follows:

5'-

GGGGACAAGTTTGTACAAAAAAGCAGGCTCCACCATGGTGAGCAAGGGCG

AG-3'
(forward);
and

5'-

GGGGACCACTTTGTACAAGAAAGCTGGGTTGGCTGATTATGATCTAGAG-

3'
(reverse)

Figure 3:
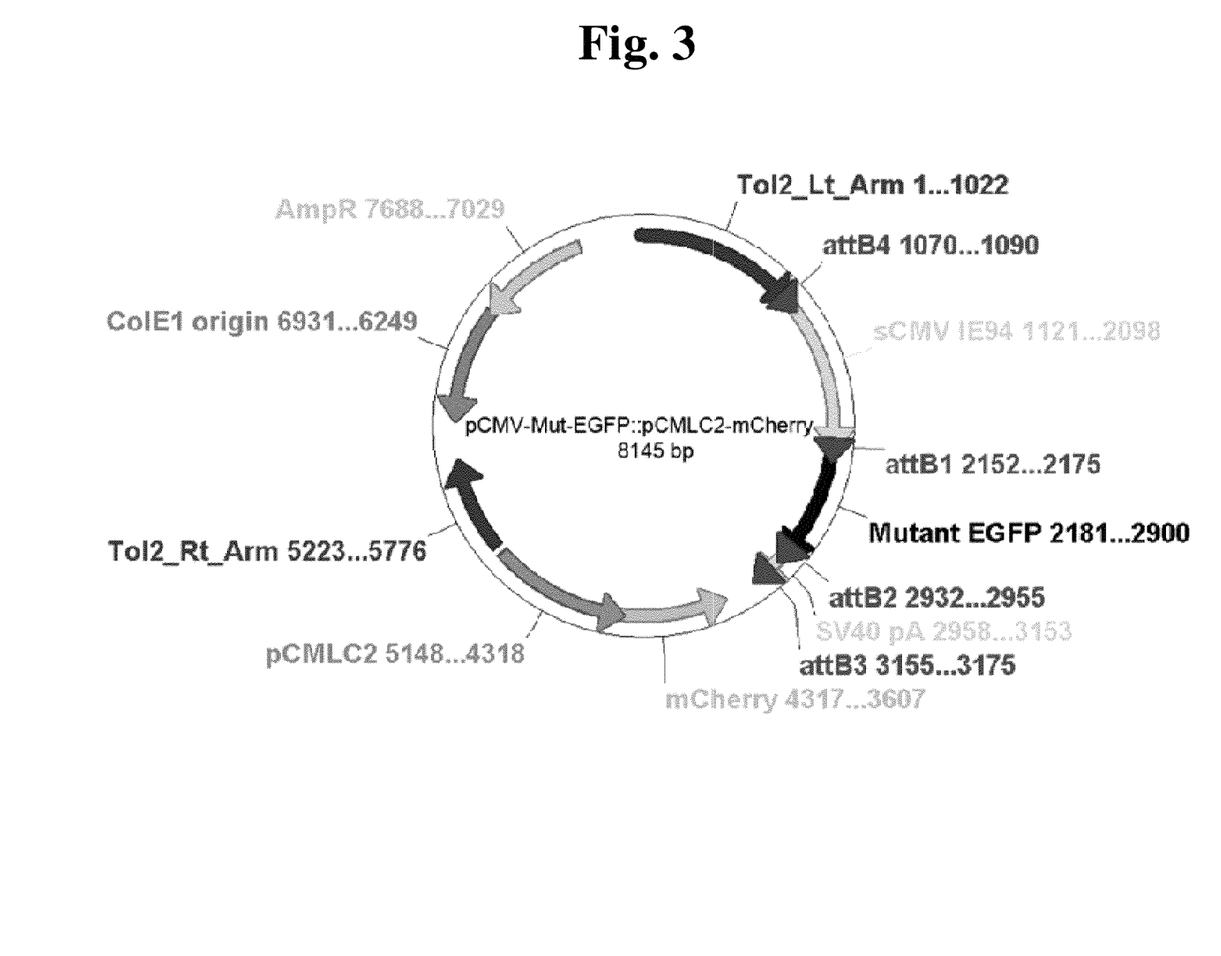
FIG. 3 is a map of pCMV-Mut-EGFP::pCMLC2-mCherry vector. EGFP$^{mut}$ DNA was cloned between two att sites in tol2kit.

The resulting PCR product was gateway-cloned into Tol2 plasmid such that the EGFP$^{mut}$ gene was driven by CMV promoter (The Tol2kit: a multisite gateway-based construction kit for Tol2 transposon transgenesis constructs (Fisher, et al., 2006; Kwan, et al., 2007). The Tol2 plasmid also harbors mCherry gene driven by heart-specific CMLC2 promoter, which can be used as an indicator of germline transmission. The resulting construct, pCMV-Mut-EGFP::pCMLC2-mCherry (FIG. 3), was verified by restriction enzyme digestion and DNA sequencing.

Generation of Transgenic Zebrafish.

EGFP$^{mut}$ plasmid constructed as described above was microinjected into one-cell stage fertilized eggs laid by the AB* zebrafish line (Oregon University, Corvallis, Oreg.) with transposase mRNA. The microinjected eggs were raised to sexual maturity and mated to wild type AB* zebrafish. Subsequently, the resulting embryos were screened for the presence of mCherry fluorescence in the heart. The screened embryos (hereinafter named as F1) were processed for RT-PCR, Western blotting and Southern blotting to verify the genomic integration of mutant EGFP. The F1 embryos were raised again to sexual maturity and mated to each other to generate F2 embryos homozygous for EGFP$^{mut}$. F3 embryos, generated by in-cross between F2 zebrafish, were raised again to sexual maturity.

Treatment with Mutagens

Fertilized eggs were obtained by pair mating transgenic F3 female and nontransgenic male fish. We divided 24 hr embryos, still coated with chorion, into three groups (266 embryos/group) and exposed them for 30 min at 26° C. to 10 ml of 0, 2, or 5 mM ENU in 0.1% Instant Ocean salts (Senja Pharmaceutical, Hyogo, Japan). Mutagenized embryos were then rinsed and kept in a 28.5° C. incubator for three days. Almost all embryos were hatched during this incubation period. The pooled surviving larvae were checked for morphological abnormality and EGFP$^+$ larvae were selected and then scored by FACSAria (BD Biosciences).

Statistical Analysis

All analyses were conducted using the SPSS for Windows statistical package, version 11.0. The statistical analysis of experimental values in the Ames test was used by parametric methods—Dunnett's t-test (Dunnett, 1955; Dunnett, 1964) and linear regression for looking at dose-response (Kirkland, 1994). The statistical analysis in the SCE test was performed by one-way analysis of variance (ANOVA) and, subsequently, by Student's t-test and post-hoc Dunnett's t-test. The analysis of TF was performed using the $\chi^2$-test. A p-value of ≤0.05 was considered as indicative of statistical significance for all tests used.

Results

Construction of Non-Fluorescing EGFP

Figure 4:
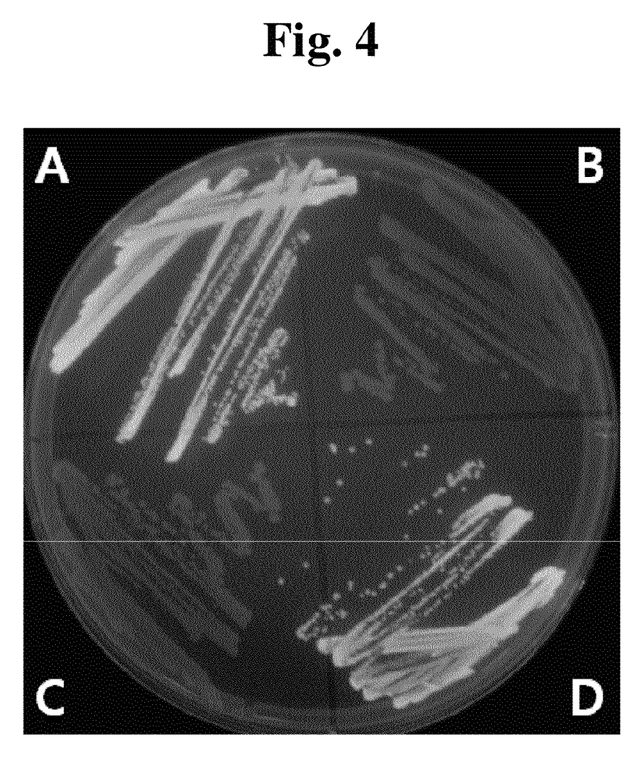
FIG. 4 represents a fluorescence observation in *Salmonella* LT2 strain carrying EGFP variant plasmids under UV light. The plasmid used is as follows: A, pEGFP::cat; B, pEGFP$^{mut1}$::cat; C. pEGFP$^{mut3}$::cat; D. pEGFP$^{mut2}$::cat.

In an attempt to create a visual genotoxicity test system using EGFP that is genetically analogous to Ames test, we paid attention to two mutations adopted in the Ames test, hisG46 (TA100) and hisD6610 (TA97). The hisG46 mutation carries Leu (CTC) to Pro (CCC) base pair substitution. The hisD6610 carries C1 frameshift mutation resulting in a run of six cytosines (—C—C—C—C—C—C—). This mutation is sensitive to some of the mutagens that revert −1 frameshift mutation of hisD3052 (TA98) which affects the reading frame of a nearby repetitive —C-G-C-G-C-G-C-G-sequence (Isono and Yourno, 1974; Levin, Yamasaki, et al., 1982). We used site-directed mutagenesis to generate analogous mutations in EGFP that should result in non-fluorescing protein. First, we substituted Leu$^{137}$ with Pro similarly as hisG46 mutation. This substitution rendered the mutant EGFP to non-fluorescent (FIG. 4). This was named as EGFP$^{mut1}$ and was expected to be suitable to detect basepair substitution by mutagens as hisG46. Next, we created another mutant EGFP that GGG (Gly) was added next to Gly$^{51}$ (GGG), which is located in the α-helix region bound to β-barrel, eleven of which form a hollow cylinder of core structure of GFP (reviewed in Tsien, 1998). Additional glycine next to Gly$^{51}$ (GGG) therefore was least likely to perturb the EGFP molecule resulting in fluorescent protein. FIG. 4 shows the fluorescing EGFP protein with additional Gly, EGFP$^{mut2}$. Afterwards, a hotspot DNA sequence with a run of 6 guanosines for frameshift mutation was created. Consequently, −1G frameshift mutation (with 5 guanosines) was created from EGFP$^{mut2}$ to produce EGFP$^{mut3}$. In this case, EGFP protein translation would be stopped after 62$^{nd}$ amino acid, ten amino acids after Gly$^{51}$. This protein was found to be nonfluorescent (FIG. 4). EGFP$^{mut3}$ carrying run of 5 guanosines was expected to be analogous to the hisD6610, a strain used to detect frameshift mutations.

Genotoxicity Test Using Salmonella typhimurium Test Strains Carrying EGFP$^{mut}$ Subsequently, the gene for EGFP$^{mut}$ was placed in the chromosome of relevant Salmonella typhimurium to establish mutation test strains analogous to that of Ames test. Linear DNA transformation method using λ Red system (Datsenko and Wanner, 2000) was employed to place the EGFP$^{mut}$ genes at putAP sites (Elliott, 1992) in the wild type Salmonella chromosome, LT2. Then, each EGFP$^{mut1}$ and EGFP$^{mut3}$ gene was moved to TA100 and TA98 using generalized transducing phage, P22, resulting in a construction of CH 4001 and 4003.

We tested mutation frequency of these two strains together with conventional Ames test strains, TA100 and TA98, in the presence of mutagens, ENU and ICR191. ENU is known to induce base-pair substitution while ICR191 frameshift mutation (OECD, 1997). His$^+$ revertants were selected on minimal plates and EGFP$^+$ revertants were screened on NA plates which allowed visualization of about 10$^6$ colonies individually. In the absence of mutagen, both His$^+$ or EGFP$^+$ revertants arose at the frequency of 1.1–1.8×10$^{-6}$ in TA strains and CH strains (Table 3). In the presence of 0.1 mg/plate of ENU, the frequency of His$^+$ revertants in TA100 and CH4001, test strains for base substitutions, increased to 5.6×10$^{-6}$ and 5.2×10$^{-6}$, respectively. This reversion frequency is within the range reported previously (Lang, 1984). Most interestingly, we found the EGFP$^+$ reversion in the presence of ENU also increased similarly, to the frequency of 7.1×10$^{-6}$. CH1003, a test strain for frameshift mutation, together with TA98, was incubated with 1 mg/plate ICR191. The His$^+$ revertants increased in CH4003 with mutation frequency of 420.8×10$^{-6}$ similarly as previously reported (Hera and Pueyo, 1988). The His$^+$ revertants in TA98 also increased with the frequency of 327.6×10$^{-6}$. In the presence of ICR191, EGFP$^+$ revertants increased similarly with the frequency of 456.3×10$^{-6}$. Taken together, these results indicate that the CH4001 and CH4003 are functionally analogous to TA100 and TA98 for His$^+$ reversion, respectively. Therefore, the EGFP reversion system of CH strains could substitute His$^+$ reversion system of Ames test.

TABLE 3

Number of revertants from Salmonella tester strains*

| Treatment** | TA100 | EGFP$^{mut1}$ | TA100 | TA98 | EGFP$^{mut2}$ | TA98 |
|---|---|---|---|---|---|---|
| | His$^+$ | His$^+$ | EGFP$^+$ | His$^+$ | His$^+$ | EGFP$^+$ |
| None | 1.6 | 1.8 | 1.2 | 1.1 | 1.2 | 0.5 |
| ENU | 5.6 | 5.2 | 7.1 | 3.2 | 3.5 | 3.2 |
| ICR191 | — | — | — | 420.8 | 377.6 | 456.3 |

*Total 10$^6$ bacteria were plated on minimal media plates for screening His$^+$ revertants and NA plates for EGFP$^+$ revertants. EGFP$^{mut1}$ carried L137P amino acid substitution and EGFP$^{mut2}$ carried frameshift mutation at G$^{51}$G$^{52}$ mutant construct.
**0.1 mg/plate and 1 mg/plate of ENU and ICR191 were tested, respectively.

Genotoxicity Test Using Transgenic Zebra Fish Carrying EGFP$^{mut}$ Gene

We injected Tol2 plasmid encoding EGFP$^{mut}$ and transposase mRNA into one-cell stage fertilized zebrafish eggs. F1 progeny with germline transmission were selected by PCR and Southern blot analysis as described in the Experimental Protocol. One highly transgene-positive line was established. When the F3 progeny of this line were obtained by pair mating F2 fish with nontransgenic fish, the F2 fish transmitted the transgene to about 50% of F3 progeny fish, indicating that the transgene had been stably integrated into one of the zebrafish chromosomes. As a result, we established MutaFish$^1$ and MutaFish$^3$ carrying EGFP$^{mut1}$ and EGFP$^{mut3}$, respectively.

To evaluate whether these transgenic fishes could detect mutations in vivo, 24 hr embryos obtained by pair mating the transgenic and nontransgenic fish were treated with mutagens for 30 min: MutaFish$^1$ with ENU (5 mM) and MutaFish$^3$ with ICR191 (10 mM). Three days after treatment, the number of EGFP$^+$ larvae was determined (Table 4). Background mutant frequency in the absence of mutagen was about 2–3×10$^{-5}$. This value, which was similar to that observed for the mouse system (Gondo, Shioyama, et al., 1996) and transgenic zebrafish carrying rpIS (Amanuma, Takeda, et al., 2000), was sufficiently low to detect mutations in the genomic DNA of the treated embryos. Treatment of MutaFish$^1$ with ENU led to increase in the number of EGFP$^+$ larvae with frequency of 6.3×10$^{-4}$, which was correlated with the increase in morphological abnormality, 20.9%. This is analogous to the observation with transgenic zebrafish carrying rpIS (Amanuma, Takeda, et al., 2000). Treatment of MutaFish$^3$ with ICR191 led to increase in number of EGFP$^+$ larvae with frequency of 2.32×10$^{-3}$, which was correlated with the increase in morphological abnormality, 24.2%. Taken together, these data indicated that MutaFish system could be employed to quantify genotoxicity of mutagenic compounds including alkylating agents and base adducts.

TABLE 4

Mutation frequency of the transgene in embryo treated with mutagens*

| | EGFP$^{mut1}$ MutaFish | | | EGFP$^{mut2}$ MutaFish | | |
|---|---|---|---|---|---|---|
| Treatment** | Survival rate (%) | Morphological abnormality (%) | Mutant frequency × $10^{-5}$ | Survival rate (%) | Morphological abnormality (%) | Mutant frequency × $10^{-5}$ |
| none | 100 | 0.075 | 2 | 100 | 0.081 | 3 |
| ENU | 97.3 | 20.9 | 63 | — | — | — |
| ICR191 | — | — | — | 79.2 | 24.2 | 232 |

*Total $10^6$ fishes were examined for EGFP expression, EGFP$^{mut1}$ MutaFish carried L137P amino acid substitution and EGFP$^{mut2}$ MutaFish carried frameshift mutation at $G^{51}G^{52}$ mutant construct.
**5 mM and 10 mM of ENU and ICR191 were tested, respectively.

DISCUSSION

MutaFish using EGFP reversion system would provide an alternative animal test for genotoxicity tests. The biggest advantage of MutaFish system would be the visualization of genotoxicity: the quantification of EGFP$^+$ larvae under UV light would be the reflection of genotoxicity of chemical compounds and no additional manipulation of the larvae is needed. Within the regulatory system to register pharmaceuticals, there is a requirement for genotoxicity tests (Billinton, Hastwell, et al., 2008; CPM/ICH 1995), designed to identify compounds that might damage or in other ways alter the genome and hence pose a carcinogenicity and/or heritable mutation hazard. Although various alternative approaches for predicting environmental risks of chemicals are available, we demonstrated here that MutaFish would be the most convenient animal assay system. The zebrafish is unique with respect to the level of available knowledge, technology and approaches. However, this visual technology of EGFP$^{mut}$ system applied to the zebrafish would also be applicable to other experimental model fish species such as the medaka (*Oryzias latipes*) and fathead minnow (*Pimephales promelas*). Larvae of these species have also been suggested as a method to replace acute toxicity tests with juvenile/adult fish (Braunbeck, Boettcher, et al., 2005; Scholz, Fischer, et al., 2008).

In order to improve the sensitivity of MutaFish system, the fish with defect in DNA repair enzyme must be considered in the future. In a number of in vivo murine models, following stains have been developed and shown to detect more efficiently various noxious chemical compounds: XPA$^{-/-}$, XPC$^{-/-}$, Msh2$^{+/-}$, Msh2$^{-/-}$ and p53$^{+/-}$ mutants, Apc mutant mice (ApcΔ716, Apc1638N, Apcmin), and A33Δ_β-cat knock-in mice (Dashwood, 2003). Several of these models have provided insights into the mutation spectra induced in vivo by chemical compounds in target and non-target organs for tumorigenesis. In addition, other genes, yet unidentified, involved in DNA repair system should also be tested in MutaFish for further increase in the sensitivity of detection.

Although we have taken advantage of fluorescent GFP in this study, the technology should be extended to other fluorescent proteins including the battery of GFP variants (Shaner, Steinbach, et al., 2005) and light generating proteins (REF) including firefly luciferase and renila luciferase. It is possible that there might be other mutations in GFP, not described in this study, that obliterate fluorescence, have higher reversion rate upon exposure to chemicals than currently described ones.

Over the past few years, zebrafish have become an increasingly important tool for biologists as a model to study development because their embryos are transparent and develop quickly, their genes are highly conserved (around 75%) with humans and they are vertebrate (Bradbury, 2004; Scholz, Fischer, et al., 2008). The fact that the developing embryo is highly sensitive to a toxic insult makes the zebrafish system an attractive in vivo model to visualize genotoxicity of chemical compounds. According to current European Union legislation for the protection of animals used for experimental and other scientific purposes, the use of embryonic stages of vertebrates is not regulated (Commission of the European Communities, 1986). Hence, experiments with embryos are considered as an alternative to animal experiments (Fleming, 2007). Thus, MutaFish system represents an attractive model for environmental risk assessment of chemicals since it offers the possibility to perform small-scale, high-throughput analyses using a modified flow cytometry method.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

Amanuma, K., H. Takeda, et al., (2000). "Transgenic zebrafish for detecting mutations caused by compounds in aquatic environments." *Nat Biotechnol*, 18 (1): 62-5.

Ames, B. N., W. E. Durston, et al., (1973). "Carcinogens are mutagens: a simple test system combining liver homogenates for activation and bacteria for detection." *Proc Natl Acad Sci USA*, 70 (8): 2281-5.

Billinton, N., P. W. Hastwell, et al., (2008). "Interlaboratory assessment of the GreenScreen HC GADD45a-GFP genotoxicity screening assay: an enabling study for independent validation as an alternative method." *Mutat Res*, 653 (1-2): 23-33.

Bradbury, J. (2004). "Small fish, big science." *PLoS Biol*, 2 (5): E148.

Braunbeck, T., M. Boettcher, et al., (2005). "Towards an alternative for the acute fish LC(50) test in chemical assessment: the fish embryo toxicity test goes multi-species—an update." *ALTEX*, 22 (2): 87-102.

Dashwood, R. H. (2003). "Use of transgenic and mutant animal models in the study of heterocyclic amine-induced mutagenesis and carcinogenesis." *J Biochem Mol Biol*, 36 (1): 35-42.

Datsenko, K. A. and B. L. Wanner (2000). "One-step inactivation of chromosomal genes in *Escherichia coli* K-12 using PCR products." *Proc Natl Acad Sci USA*, 97 (12): 6640-5.

Davis, R. W., D. Botstein, J. R. Roth (1980). *Advanced Bacterial Genetics: A manual for genetic Engineering*. NY, Cold Spring Harbor Laboratory Press.

Dunnett, C. W. (1955). "A Multiple Comparison Procedure for Comparing Several Treatments with a Control" *Journal of the American Statistical Association*, 50 (272): 1096-1121.

Dunnett, C. W. (1964). "New Tables for Multiple Comparisons with a Control" *Biometrics*, 20 (3): 482-491.

Elliott, T. (1992). "A method for constructing single-copy lac fusions in *Salmonella typhimurium* and its application to the hemA-prfA operon." *J Bacteriol*, 174 (1): 245-53.

Fisher, S., E. A. Grice, et al., (2006). "Evaluating the biological relevance of putative enhancers using Tol2 transposon-mediated transgenesis in zebrafish." *Nat Protoc*, 1 (3): 1297-305.

Fleming, A. (2007). "Zebrafish as an alternative model organism for disease modelling and drug discovery: implications for the 3Rs." NC3Rs www.nc3rs.org.uk(10).

Gondo, Y., Y. Shioyama, et al., (1996). "A novel positive detection system of in vivo mutations in rpsL (strA) transgenic mice." *Mutat Res*, 360 (1): 1-14.

Gossen, J. A., W. J. de Leeuw, et al., (1989). "Efficient rescue of integrated shuttle vectors from transgenic mice: a model for studying mutations in vivo." *Proc Natl Acad Sci USA*, 86 (20): 7971-5.

Hera, C. and C. Pueyo (1988). "Response of the L-arabinose forward mutation assay of *Salmonella typhimurium* to frameshift-type mutagens." *Mutat Res*, 203 (1): 39-45.

Isono, K. and J. Yourno (1974). "Chemical carcinogens as frameshift mutagens: *Salmonella* DNA sequence sensitive to mutagenesis by polycyclic carcinogens." *Proc Natl Acad Sci USA*, 71 (5): 1612-7.

Joseph Sambrook, D. W. R. (2001). Molecular Cloning a laboratory manual. New York, Cold Spring Harbor laboratory Press. 3.

Kirkland, D. J. (1994). "Statistical evaluation of mutagenicity test data: recommendations of the U.K. Environmental Mutagen Society." *Environ Health Perspect*, 102 Suppl 1: 43-7.

Kohler, S. W., G. S. Provost, et al., (1991). "Spectra of spontaneous and mutagen-induced mutations in the lad gene in transgenic mice." *Proc Natl Acad Sci USA*, 88 (18): 7958-62.

Kwan, K. M., E. Fujimoto, et al., (2007). "The Tol2kit: a multisite gateway-based construction kit for Tol2 transposon transgenesis constructs." *Dev Dyn*, 236 (11): 3088-99.

Lang, R. (1984). "The mammalian spot test and its use for testing of mutagenic and carcinogenic potential: experience with the pesticide chlordimeform, its principal metabolites and the drug lisuride hydrogen maleate." *Mutat Res*, 135 (3): 219-24.

Levin, D. E., E. Yamasaki, et al., (1982). "A new *Salmonella* tester strain, TA97, for the detection of frameshift mutagens. A run of cytosines as a mutational hot-spot." *Mutat Res*, 94 (2): 315-30.

Maron, D. M. and B. N. Ames (1983). "Revised methods for the *Salmonella* mutagenicity test." *Mutat Res*, 113 (3-4): 173-215.

Nohmi, T., M. Katoh, et al., (1996). "A new transgenic mouse mutagenesis test system using Spi- and 6-thioguanine selections." *Environ Mol Mutagen*, 28 (4): 465-70.

Scholz, S., S. Fischer, et al., (2008). "The zebrafish embryo model in environmental risk assessment—applications beyond acute toxicity testing." *Environ Sci Pollut Res Int*, 15 (5): 394-404.

Shaner, N. C., P. A. Steinbach, et al., (2005). "A guide to choosing fluorescent proteins." *Nat Methods*, 2 (12): 905-9.

Tsien, R. Y. (1998). "The green fluorescent protein." *Annu Rev Biochem*, 67: 509-44.

W. Barnes, E. T., E. Eisenstadt (1982). "Base-sequence analysis of His$^+$ revertants of the hiG46 missense mutation in *Salmonella typhimurium*." *Environ. Mutagen*, 4 (3): 297 (abstr. Aa-1).

Yang, T. T., L. Cheng, et al., (1996). "Optimized codon usage and chromophore mutations provide enhanced sensitivity with the green fluorescent protein." *Nucleic Acids Res*, 24 (22): 4592-3.

What is claimed is:

1. A method for determining the genotoxicity of a test substance, comprising the steps of:
    (a) transforming a zebrafish with a nucleotide sequence encoding a non-fluorescing mutant form of EGFP (enhanced green fluorescent protein) comprising one of the sequences selected from the group consisting of SEQ ID NO:3 and SEQ ID NO:4;
    (b) treating the transformed zebrafish with a test substance; and
    (c) measuring fluorescence in the test substance-treated zebrafish, wherein the fluorescence is generated by reversion of the non-fluorescing EGFP to fluorescent EGFP due to a back mutation of the nucleotide sequence in the test substance-treated zebrafish.

2. The method of claim 1, wherein the non-fluorescing mutant EGFP is prepared by (i) a frameshift mutation or (ii) a missense mutation-producing substitution mutation in a nucleotide sequence of a wild type fluorescent EGFP.

3. The method of claim 1, wherein the back mutation reverts the non-fluorescing mutant EGFP to the fluorescent EGFP with the frameshift mutation.

4. The method of claim 1, wherein the back mutation the non-fluorescing mutant EGFP to the fluorescent EGFP with the substitution mutation.

5. The method of claim 1, wherein the transformed zebrafish to be treated with the test substance is an embryo.

6. The method of claim 5, wherein the method further comprises the step of obtaining a fry larvae by hatching the transformed zebrafish derived embryo after step (b).

7. The method of claim 1, wherein step (c) is carried out in the test substance-transformed fish by flow cytometry.

8. The method of claim 6, wherein step (c) is carried out in the fry larvae obtained by hatching the transformed zebrafish derived embryo through flow cytometry.

9. The method of claim 1, wherein the non-fluorescing mutant EGFP is encoded by SEQ ID NO:1.

10. The method of claim 1, wherein the non-fluorescing mutant EGFP is encoded by SEQ ID NO:2.

11. The method of claim 1, wherein the non-fluorescing mutant EGFP comprises the sequence of SEQ ID NO:3.

12. The method of claim 1, wherein the non-fluorescing mutant EGFP comprises the sequence of SEQ ID NO:4.

13. A isolated nucleotide sequence comprising the sequence of SEQ ID NO:1 or SEQ ID NO:2 or the complementary sequence thereof.

14. An isolated protein comprising the sequence of SEQ ID NO:3 or the sequence of SEQ ID NO:4.

* * * * *

SEQUENCE LISTING

```
<160> NUMBER OF SEQ ID NOS: 16

<210> SEQ ID NO 1
<211> LENGTH: 720
<212> TYPE: DNA
<213> ORGANISM: Artificial Sequence
<220> FEATURE:
<223> OTHER INFORMATION: EGFP mutant 1

<400> SEQUENCE: 1
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat ccccgggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
```

```
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtaa   720
```

<210> SEQ ID NO 2
<211> LENGTH: 722
<212> TYPE: DNA
<213> ORGANISM: Artificial Sequence
<220> FEATURE:
<223> OTHER INFORMATION: EGFP mutant 3

<400> SEQUENCE: 2

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga cccctgaagtt catctgcacc accgggggaa gctgcccgtg ccctggccca   180
ccctcgtgac caccctgacc tacggcgtgc agtgcttcag ccgctacccc gaccacatga    240
agcagcacga cttcttcaag tccgccatgc ccgaaggcta cgtccaggag cgcaccatct    300
tcttcaagga cgacggcaac tacaagaccc gcgccgaggt gaagttcgag ggcgacaccc    360
tggtgaaccg catcgagctg aagggcatcg acttcaagga ggacggcaac atccccgggc    420
acaagctgga gtacaactac aacagccaca acgtctatat catggccgac aagcagaaga    480
acggcatcaa ggtgaacttc aagatccgcc acaacatcga ggacggcagc gtgcagctcg    540
ccgaccacta ccagcagaac ccccccatcg gcgacggccc cgtgctgctg cccgacaacc    600
actacctgag cacccagtcc gccctgagca agacccccaa cgagaagcgc gatcacatgg    660
tcctgctgga gttcgtgacc gccgccggga tcactctcgg catggacgag ctgtacaagt    720
aa                                                                   722
```

<210> SEQ ID NO 3
<211> LENGTH: 239
<212> TYPE: PRT
<213> ORGANISM: Artificial Sequence
<220> FEATURE:
<223> OTHER INFORMATION: EGFP mutant 1

<400> SEQUENCE: 3

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Pro Gly His Lys Leu Glu Tyr
    130                 135                 140

Asn Tyr Asn Ser His Asn Val Tyr Ile Met Ala Asp Lys Gln Lys Asn

```
                       145                 150                 155                 160
Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 4
<211> LENGTH: 62
<212> TYPE: PRT
<213> ORGANISM: Artificial Sequence
<220> FEATURE:
<223> OTHER INFORMATION: EGFP mutant 3

<400> SEQUENCE: 4

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Gly Ser Cys Pro Cys Pro Gly Pro Pro Ser
    50                  55                  60

<210> SEQ ID NO 5
<211> LENGTH: 20
<212> TYPE: DNA
<213> ORGANISM: Artificial Sequence
<220> FEATURE:
<223> OTHER INFORMATION: mEGFP-F primer

<400> SEQUENCE: 5
cctgcaggtc gactctagag                                              20

<210> SEQ ID NO 6
<211> LENGTH: 20
<212> TYPE: DNA
<213> ORGANISM: Artificial Sequence
<220> FEATURE:
<223> OTHER INFORMATION: mEGFP-R primer

<400> SEQUENCE: 6
ccggcgctca gttggaattc                                              20

<210> SEQ ID NO 7
<211> LENGTH: 33
<212> TYPE: DNA
<213> ORGANISM: Artificial Sequence
<220> FEATURE:
<223> OTHER INFORMATION: G51GGG-F primer

<400> SEQUENCE: 7
atctgcacca ccggggggaa gctgcccgtg ccc                               33

<210> SEQ ID NO 8
<211> LENGTH: 33
<212> TYPE: DNA
<213> ORGANISM: Artificial Sequence
```

```
<220> FEATURE:
<223> OTHER INFORMATION: G51GGG-R primer

<400> SEQUENCE: 8
gggcacgggc agcttccccc cggtggtgca gat                                33

<210> SEQ ID NO 9
<211> LENGTH: 35
<212> TYPE: DNA
<213> ORGANISM: Artificial Sequence
<220> FEATURE:
<223> OTHER INFORMATION: G51GGG+G-F primer

<400> SEQUENCE: 9
catctgcacc accggggggg aagctgcccg tgccc                              35

<210> SEQ ID NO 10
<211> LENGTH: 35
<212> TYPE: DNA
<213> ORGANISM: Artificial Sequence
<220> FEATURE:
<223> OTHER INFORMATION: G51GGG+G-R primer

<400> SEQUENCE: 10
gggcacgggc agcttccccc ccggtggtgc agatg                              35

<210> SEQ ID NO 11
<211> LENGTH: 33
<212> TYPE: DNA
<213> ORGANISM: Artificial Sequence
<220> FEATURE:
<223> OTHER INFORMATION: L137P-F primer

<400> SEQUENCE: 11
ctcgtgacca ccctggccta cggcgtgcag tgc                                33

<210> SEQ ID NO 12
<211> LENGTH: 33
<212> TYPE: DNA
<213> ORGANISM: Artificial Sequence
<220> FEATURE:
<223> OTHER INFORMATION: L137P-R primer

<400> SEQUENCE: 12
gcactgcacg ccgtaggcca gggtggtcac gag                                33

<210> SEQ ID NO 13
<211> LENGTH: 79
<212> TYPE: DNA
<213> ORGANISM: Artificial Sequence
<220> FEATURE:
<223> OTHER INFORMATION: lacP-EGFPmut::CAT forward primer

<400> SEQUENCE: 13
gaaatcgcct gttaatggta ccaatagcct tgacgcaata gagtaatgac tcactcactc   60
attaggcacc ccaggcttt                                                79

<210> SEQ ID NO 14
<211> LENGTH: 76
<212> TYPE: DNA
<213> ORGANISM: Artificial Sequence
<220> FEATURE:
<223> OTHER INFORMATION: lacP-EGFPmut::CAT reverse primer

<400> SEQUENCE: 14
cgtcattgtc agtctcttac agaaagatta cacgattatt tcatcggcag gagacgcgta   60
```

```
gcaccaggcg tttaag                                                         76

<210> SEQ ID NO 15
<211> LENGTH: 52
<212> TYPE: DNA
<213> ORGANISM: Artificial Sequence
<220> FEATURE:
<223> OTHER INFORMATION: attB1 primer

<400> SEQUENCE: 15
ggggacaagt ttgtacaaaa aagcaggctc caccatggtg agcaagggcg ag                 52

<210> SEQ ID NO 16
<211> LENGTH: 49
<212> TYPE: DNA
<213> ORGANISM: Artificial Sequence
<220> FEATURE:
<223> OTHER INFORMATION: attB2 primer

<400> SEQUENCE: 16
ggggaccact ttgtacaaga aagctgggtt ggctgattat gatctagag                     49
```